United States Patent [19]

Belanger et al.

[11] Patent Number: 4,728,735
[45] Date of Patent: Mar. 1, 1988

[54] 10,11-DIHYDRO-DIBENZO-[B,F][1,4]-THIAZEPIN DERIVATIVES

[75] Inventors: Patrice C. Belanger, Dollard des Ormeaux; Joshua Rokach, Laval; John Scheigetz, Dollard des Ormeaux, all of Canada

[73] Assignee: Merck & Co., Inc., Rahway, N.J.

[21] Appl. No.: 928,747

[22] Filed: Nov. 10, 1986

Related U.S. Application Data

[63] Continuation of Ser. No. 660,596, Oct. 15, 1984, abandoned.

[51] Int. Cl.$^4$ .................. A61K 31/55; C07D 281/16
[52] U.S. Cl. ........................................ 540/488; 540/547
[58] Field of Search .................. 540/488, 547; 514/211

[56] References Cited

U.S. PATENT DOCUMENTS

| | | | |
|---|---|---|---|
| 3,539,573 | 11/1970 | Schmutz et al. | 260/330 |
| 3,860,606 | 1/1975 | Van Der Burg | 260/309.7 |
| 4,263,207 | 4/1981 | Rokach | 260/330 |

FOREIGN PATENT DOCUMENTS 84300239.5 12/1983 European Pat. Off. ............. 544/35

OTHER PUBLICATIONS

Schmutz et al, C.A., vol. 69, 1968 69: 36193(d) p. 3386.
Schmutz et al, C.A., vol. 69, 1968 69: 36195(f) p. 3386.
Shen et al, The Development of Antiasthmatic Drug Part III, ed, Butterworth Publishers, Kent, England pp. 315–336.

*Primary Examiner*—Henry R. Jiles
*Assistant Examiner*—J. G. Mullins
*Attorney, Agent, or Firm*—Charles M. Caruso; Hesna J. Pfeiffer

[57] ABSTRACT

Compounds of the Formula I:

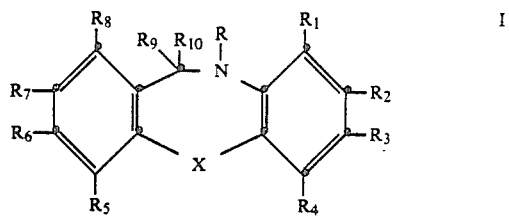

are inhibitors of the mammalian 5-lipoxygenase enzyme system of the arachidonic acid cascade. As such, these compounds are useful therapeutic agents for treating allergic conditions, asthma, cardiovascular disorders and inflammation and are useful as cytoprotective agents.

11 Claims, No Drawings

10,11-DIHYDRO-DIBENZO-[B,F][1,4]-THIAZEPIN DERIVATIVES

This is a continuation of application Ser No. 660,596, filed Oct. 5, 1984, now abandoned.

This invention is directed to inhibitors of the 5-lipoxygenase enzyme system of the arachidonic acid cascade. Inhibition of 5-lipoxygenase prevents the biosynthesis of the leukotrienes.

The leukotrienes are a novel group of biologically active mediators derived from arachidonic acid through the action of lipoxygenase enzyme systems. There are two groups of leukotrienes derived from the common unstable precursor Leukotriene $A_4$. The first of these are the peptido-lipid leukotrienes, the most important being Leukotrienes $C_4$ and $D_4$. These compounds collectively account for the biologically active material known as the slow reacting substance of anaphylaxis.

The leukotrienes are potent smooth muscle contracting agents, particularly on respiratory smooth muscle but also on other tissues (e.g. gall bladder). In addition, they promote mucous production, modulate vascular permeability changes and are potent inflammatory agents in human skin. The most important compound in the second group of leukotrienes is Leukotriene $B_4$, a dihydroxy fatty acid. This compound is a potent chemotactic agent for neutrophils and eosinophils and in addition, may modulate a number of other functions of these cells. It also effects other cell types such as lymphocytes and for example may modulate the action of T-suppressor cells and natural killer cells. When injected in vivo, in addition to promoting the accumulation of leukocytes, Leukotriene $B_4$ is also a potent hyperalgesic agent and can modulate vascular permeability changes through a neutrophil dependent mechanism. Both groups of leukotrienes are formed following oxygenation of arachidonic acid through the action of a 5-lipoxygenase enzyme. See for example, D. M. Bailey et al., Ann. Rpts. Med. Chem. 17 203 (1982).

The leukotrienes are potent spasmogens of human trachea, bronchus and lung parenchymal strips, and when administered to normal volunteers as aerosols are 3,800 times more potent that histamine at inducing a 50% decrease in air flow at 30% of vital capacity. They mediate increases in vascular permeability in animals and promote mucous production in human bronchial explants. In addition, Leukotriene $B_4$ may also mediate mucous production and could be an important mediator of neutrophil and eosinophil accumulation in asthmatic lungs. 5-lipoxygenase products are also thought to be regulators of mast cell degranulation and recent studies with human lung mast cells have suggested that 5-lipoxygenase inhibitors, but not corticosteroids, may suppress antigen-induced mast cell degranulation. In vitro studies have shown that antigen challenge of human lung results in the release of leukotrienes and in addition purified human mast cells can produce substantial amount of leukotrienes. There is therefore good evidence that leukotrienes are important mediators of human asthma. 5-lipoxygenase inhibitors would therefore be a new class of drugs for the treatment of asthma.

Psoriasis is a human skin disease which effects between two and six percent of the population. There is no adequate therapy for psoriasis and related skin conditions. The evidence for leukotriene involvement in these diseases is as follows. One of the earliest events in the development of prepapillary lesions is the recruitment of leukocytes to the skin site. Injection of Leukotriene $B_4$ into human skin results in a pronounced neutrophil accumulation. There are gross abnormalities in arachidonic acid metabolism in human psoriatic skin. In particular, highly elevated levels of free arachidonic acid can be measured as well as large amounts of lipoxygenase products. Leukotriene $B_4$ has been detected in psoriatic lesions, but not in uninvolved skin, in biologically significant amounts.

Leukotrienes can be measured in nasal washings from patients with allergic rhinitis and are greatly elevated following antigen challenge. Leukotrienes may mediate this disease through their ability to regulate mast cell degranulation, by modulating mucous production and mucociliary clearance and by mediating the accumulation of inflammatory leukocytes.

Leukotrienes can also mediate other diseases. These include atopic dermatitis, gouty arthritis and gall bladder spasms. In addition, they may have a role in cardiovascular disease because leukotrienes $C_4$ and $D_4$ act as coronary and cerebral arterial vasoconstrictors and these compounds may also have negative inotropic effects on the myocardium. In addition, the leukotrienes are important mediators of inflammatory diseases through their ability to modulate leukocyte and lymphocyte function.

It has been discovered that the compounds of the present invention are effective inhibitors of leukotriene biosynthesis via inhibition of the mammalian 5-lipoxygenase enzyme system. Thus, these compounds are useful therapeutic agents for treating conditions such as asthma, allergies, cardiovascular disorders such as angina and inflammation, for amelioration of skin diseases like psoriasis and atopic eczema, and as cytoprotective agents.

The present invention is directed to compounds having the formula I:

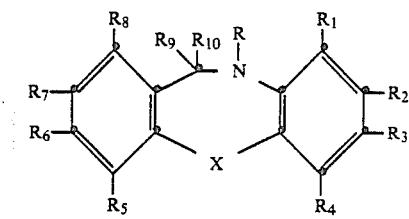

wherein:
X is thio, sulfonyl or sulfinyl;
each R is independently $C_1$ to $C_{20}$-alkyl which may be straight chain, branched chain or cyclic; perfluoro $C_1$ to $C_4$-alkyl which may be straight chain or branched; phenyl-$C_1$ to $C_4$-alkyl or $C_3$ to $C_8$-cycloalkyl-$C_1$ to $C_4$-alkyl.

$R_1$ to $R_8$ are each independently selected from hydrogen, hydroxy, halogen (including F, Cl, Br and I), —OR, OCOR, NHR, N(R)$_2$, SR, SOR, SO$_2$NHR, SO$_2$N(R)$_2$ CN, CONHR, CON(R)$_2$, COOR, CF$_3$, CF$_3$S, CHO, COR, CH$_2$OR, R, phenyl, phenyl substituted by one or more groups selected from OH, $C_1$ to $C_6$-alkyl which may be straight chain, branched or cyclic, COOR, CN, NO$_2$, CF$_3$, SR, NHR or N(R)$_2$;
$R_9$ is H or OH;
$R_{10}$ is H or together
$R_9$ and $R_{10}$ form a doubly bonded oxo group;
and pharmaceutically acceptable salts thereof.

The present invention also relates to pharmaceutical compositions containing a compound of the Formula I or a pharmaceutically acceptable salt thereof, to methods of treating mammals (especially humans), using such compounds and to methods of preparing such compounds.

A preferred group of compounds has the formula Ia:

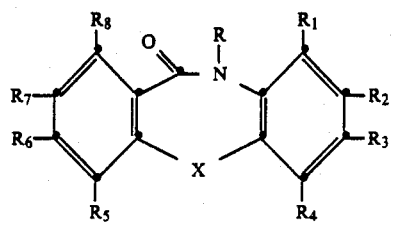

Ia

A more preferred group of compounds has the formula Ib:

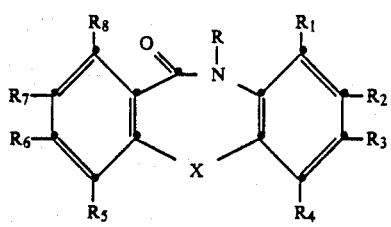

Ib wherein R is selected from $C_1$ to $C_4$-alkyl.

The preparation of compounds of the present invention is illustrated below in Schemes I, II, and III:

SCHEME I

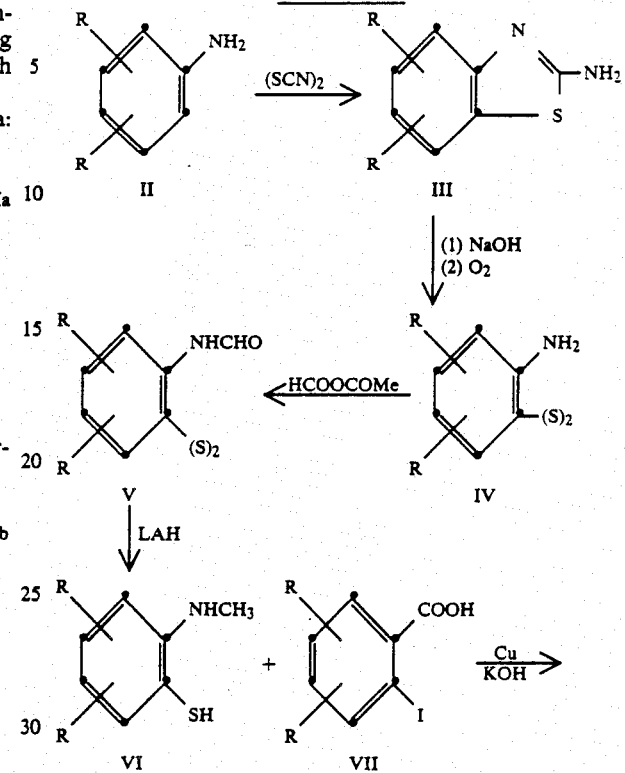

SCHEME II

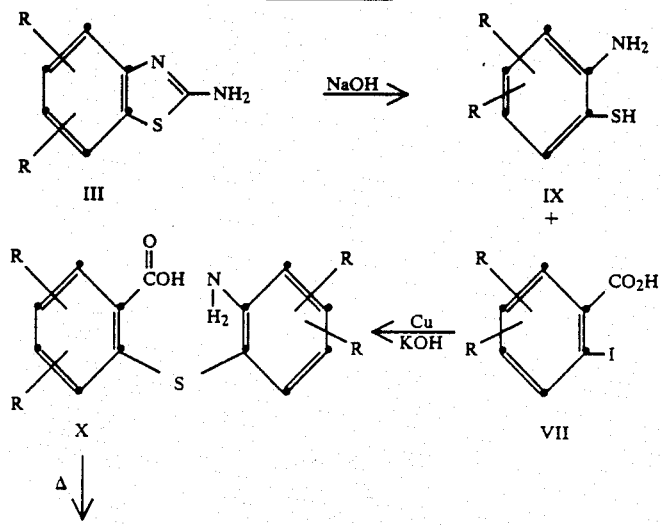

SCHEME II

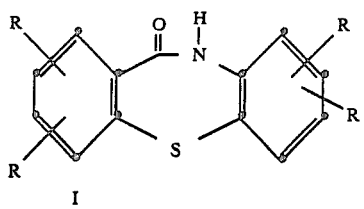

SCHEME III

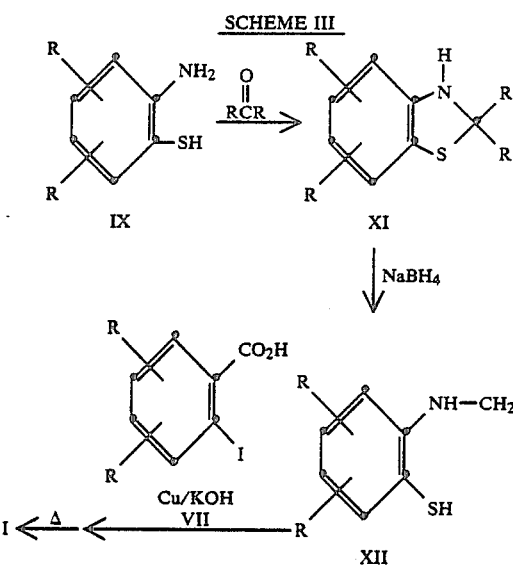

Treatment of a substituted aniline II with thiocyanogen affords the substituted 2-amino benzothiazole III. Base hydrolysis of III, using 10N KOH and refluxing overnight, affords the disulfide derivative IV which is then reacted with an anhydride or an acid chloride. The amide derivatives of structure V thus obtained are then reduced with excess lithium aluminum hydride in refluxing THF, giving rise to the properly substituted o-alkylamino thiophenol VI. Coupling of VI with a substituted ortho-iodo benzoic acid VII by refluxing in KOH/water in the presence of copper metal affords the substituted diphenyl sulfide VIII which is then heated at a temperature of 230° C. for 30 minutes under a nitrogen atmosphere to give derivatives of structure I.

For the preparation of I (R=H), the scheme outlined in Scheme II is followed. Thus, carrying out the base hydrolysis of a suitably substituted 2-amino benzothiazole under a nitrogen atmosphere affords the substituted o-amino thiophenol IX which is then coupled with a o-iodo benzoic acid VII to yield the diphenyl sulfide derivative X. Heating X at 230° C. under a nitrogen atmosphere for 30 minutes gives I (R=H).

An alternate procedure to prepare the ortho N-substituted amino thiophenol is contained in Scheme III. Reaction of ortho-amino thiophenol IX with a ketone affords the 2.2-dialkyl benzo thiazolidine XI. On reduction by NaBH₄ in ethanol, the N-alkyl thiophenol XII is obtained and, using the normal sequence, is reacted with an ortho-iodo benzoic acid VII. Thereafter, pyrolysis of the diphenyl sulfide VIII yields I.

Examples of the Formula I compounds useful in the present compositions are tabulated in Table I.

TABLE I

| Compound | Z | R | $R_3$ | $R_2$ | $R_6$ | $R_9$ | $R_{10}$ |
|---|---|---|---|---|---|---|---|
| 1 | S | H | H | H | H | =O | |
| 2 | S | H | $OCH_3$ | H | H | =O | |
| 3 | S | H | OH | H | H | =O | |
| 4 | S | H | $OCH_3$ | Cl | H | =O | |
| 5 | S | H | OH | Cl | H | =O | |
| 6 | S | H | OH | H | H | H | H |
| 7 | S | H | $OCH_3$ | H | H | H | H |
| 8 | S | CHO | $OCH_3$ | H | H | H | H |
| 9 | S | $CH_3$ | $OCH_3$ | H | H | H | H |
| 10 | $SO_2$ | H | OH | H | H | H | H |
| 11 | SO | $CH_3$ | $OCH_3$ | H | H | H | H |
| 12 | S | H | $OCH_3$ | H | H | OH | H |
| 13 | S | H | $OCH_3$ | H | $OCH_3$ | =O | |
| 14 | S | H | $OCH_3$ | H | H | =O | |
| 15 | S | H | $OC_2H_5$ | H | H | =O | |
| 16 | SO | H | $OCH_3$ | H | Cl | =O | |
| 17 | $SO_2$ | H | $OCH_3$ | H | Cl | H | H |
| 18 | $SO_2$ | H | $OCH_3$ | H | Cl | =O | |
| 19 | $SO_2$ | H | OH | H | Cl | =O | |
| 20 | $SO_2$ | H | OH | H | Cl | H | H |
| 21 | S | H | $OCH_3$ | H | $CH_3$ | =O | |
| 22 | S | $n\text{-}C_3H_7$ | $OCH_3$ | H | Cl | =O | |
| 23 | S | $n\text{-}C_3H_7$ | $OCH_3$ | H | Cl | H | H |
| 24 | S | $n\text{-}C_3H_7$ | $OCH_3$ | H | $CH_3$ | =O | |
| 25 | S | $i\text{-}C_3H_7$ | $OCH_3$ | H | H | =O | |
| 26 | S | $i\text{-}C_3H_7$ | OH | H | H | =O | |

In those instances when asymmetric centers are present, more than one stereoisomer is possible, and all possible isomeric forms are deemed to be included within the planar structural representations shown. Optically active (R) and (S) isomers may be resolved using conventional techniques known to the skilled artisan.

The following assays are useful in determining the mammalian leukotriene biosynthesis inhibiting activity and other relevant biological activites of the compounds of Formula I.

Rat Polymorphonuclear Leukocyte (P.M.N.) Assay

Rats under either anesthesia are injected (intraperitoneally) with 8 ml of a suspension of sodium caseinate (6 grams in about 50 ml water). After 15 to 24 hours the rats are sacrificed ($CO_2$) and the cells from the peritoneal cavity are recovered by lavage with 20 ml of buffer (Eagles Minimal Essential Medium containing 30 mM HERPES adjusted to pH 7.4 with NaOH). The cells are pelleted (350×g, 5 min.), resuspended in buffer with vigorous shaking, filtered through lens paper, recentrifuged and finally suspended in buffer at a concentration of 10 cells/ml. A 500 μl aliquot of the suspension (PMN) and test compound are preincubated for 2 minutes at 37° C., followed by the addition of 10 μM A-23187 calcium ionophore (Calbiochem). The suspension is stirred for an additional 4 minutes then bioassayed for LTB$_4$ content by adding an aliquot to a second 500 μl portion of the PMN at 37° C. The LTB$_4$ produced in the first incubation causes aggregation of the second PMN, is measured as a change in light transmission. The size of the assay aliquot is chosen to give a submaximal transmission change (usually −70%) for the untreated control. The percentage inhibition of LTB$_4$ formation is calculated from the ratio of transmission change in the sample to the transmission change in the compound-free control.

Antigen Challenge 'in vitro' Assay

Male guinea pigs weighing 300-350 g are sensitized by injecting (intraperitoneally) 0.5 ml of a suspension containing 0.4 mg of egg albumin (Ovalbumin, Grade V, Sigma Chemical Co.) and 4.0 g aluminum hydroxide in 19.6 ml of saline. Two weeks are permitted for sensitization to occur.

Three sensitized guinea pigs are stunned and exanguinated. The tracheas are removed, freed of adhering tissue and divided longitudinally by cutting through the cartilaginous tissue directly opposite the muscle insertion. Each opened trachea is then transected between every second cartilage. Four of the cut sections are tied together, end to end, in a series with No.7 silk thread ensuring that the tracheal muscles are all in the same vertical plane. Thus, each chain consists of tissue from three different animals.

The chain so formed is then suspended under 1 g of tension (by silk ties at each end) in a 20 ml organ bath containing 10 ml of modified[1] Krebs-Henseleit buffer solution gassed with 95% $O_2$ and 5% $CO_2$ at 37° C. Mepyramine (0.55 μg/ml) and indomethacin (2.67 μg/ml) are added to the buffer to avoid the contribution of histamine receptors and cyclooxygenase products to the contraction. To record responses one end of the tracheal chain is attached to a Gould-Statham UC-2 force displacement transducer which is connected to a Beckman Type R-dynograph. The preparations are allowed to equilibrate for one hour during which time the tissues are automatically washed (10 ml volume displacement) every 6 minutes.

[1]modified Krebs solution in grams/liter and (mM):
NaCl-6.87 (120); glucose-2.1 (11); NaHCO$_3$-2.1 (25); KCl-0.32(4.72); CaCl$_2$-0.28 (2.5);
MgSO$_4$.7H$_2$O-0.11 (0.5); KH$_2$PO$_4$-0.16 1.2); pH at bathing solution=7.35±0.05.

After the equilibration period the tissues are primed with methacholine (3 μg/ml; 1.5×10$^{-5}$M), washed and allowed to recover to baseline. The tissues are treated again with a second dose of methacholine, washed, allowed to return to baseline and washed for an additional hour.

Two chains are used as a control. These are incubated in a concentration of egg albumin sufficient to induce an average contraction of 50-80% of the methacholine response.

Each compound to be tested is added to two their baths (at a final concentration in each bath of 10 μg/ml) 15 minutes prior to challenging the fresh chains with egg albumin.

The response of the challenged tissue is expressed as a percentage of the methacholine maximum. The percentage inhibition for each compound is then calculated. Compounds which at 10 μg/ml (final concentration) inhibit the egg albumin response by 50% or more are retested at a lower concentration.

Asthmatic Rat Assay

Rats are obtained from an inbred line of asthmatic rats. Both female and male rats from 200 to 300 g are used.

Egg albumin (EA), grade V, crystallized and lyophilized, is obtained from Sigma Chemical Co., St. Louis. *Bordetella pertussis* vaccine, containing 30×10$^9$ killed bacteria per ml is obtained from the Institute Armand-Frappier, Laval des Rapides, Quebec. Aluminum hydroxide is obtained from the Regis Chemical Company, Chicago.

The challenge and subsequent respiratory recordings are carried out in a clear plastic box with internal dimensions 10×6×4 inches. The top of the box is removable; in use, it is held firmly in place by four clamps and an airtight seal is maintained by a soft rubber gasket. Through the center of each end of the chamber a Devilbiss nebulizer (No. 40) is inserted via an airtight seal and each end of the box also has an outlet. A Fleisch No. 0000 pneumotachograph is inserted into one end of the box and coupled to a Grass volumetric pressure transducer (PT5-A) which is then connected to a Beckman Type R Dynograph through appropriate couplers. While aerosolizing the antigen, the outlets are open and the pneumotachograph is isolated from the chamber. The outlets are closed and the pneumotachograph and the chamber are connected during the recording of the respiratory patterns. For challenge, 2 ml of a 3% solution of antigen in saline is placed into each nebulizer and the aerosol is generated with air from a small Potter diaphragm pump operating at 10 psi and a flow of 8 liters/minute.

Rats are sensitized by injecting (subcutaneously) 1 ml of a suspension containing 1 mg EA and 200 mg aluminum hydroxide in saline. Simultaneously, they receive an injection (intraperitoneally) of 0.5 ml of *B. pertussis* vaccine. They are used between days 14 and 18 postsensitization. In order to eliminate the serotonin component of the response, rats are pretreated intravenously 5 minutes prior to aerosol challenge with 30 gm/kg methylserzide. Rats are then exposed to an aerosol of 3% EA in saline for exactly 1 minute, then their respiratory profiles are recorded for a further 25 to 30 minutes. The duration of continuous dyspnoea is measured from the respiratory recordings.

Compounds are generally administered either intraperitoneally 1 hour prior to challenge or orally 1 and ½ hours prior to challenge. They are either dissolved in dimethylsulfoxide or suspended in 0.1% methocel and 0.5% Tween 80. The volume injected is 2 ml/kg (intraperitoneally) or 10 ml/kg (orally). Prior to oral treatment rats are starved overnight. Their activity is determined in terms of their ability to decrease the duration of symptoms of dyspnoea in comparison with a group of vehicle-treated controls. Usually, a compound is evaluated at a series of doses and an ED$_{50}$ is determined. This is defined as the dose (mg/kg) which would inhibit the duration of symptoms by 50%.

PAF-Induced Hyperalgesia Assay

Female Sprague-Dawley rats, 35 to 40 g are fasted overnight. Platelet activating factor, PAF, (L-lecithin B-acetyl O-alkyl) 1 μg/0.1 ml is given by subplantar injection in the rat paw. The compounds to be evaluated are homogenized in Aqueous Vehicle (0.9% benzyl alcohol, 0.5% Tween 80 and 0.4% methylcellulose) and administered orally in a volume of 0.1 ml, 30 minutes prior to PAF.

Animals are tested 1, 2, 3 and 4 hours after PAF administration. The vocalization threshold, defined as the pressure (mmHg) needed to evoke a squeak response, was recorded for both the injected and contralateral paw. No animal is subjected to pressure greater than 60 mmHg. Hyperalgesia is defined as a decrease in vocalization threshold as compared to a normal paw. Percent inhibition of hyperalgesia is calculated as the proportion of animals with vocalization thresholds greater than 200% of controls.

The compounds of the Formula I have unexpected activity as inhibitors of the mammalian biosynthesis of leukotriene $B_4$, as well as leukotrienes $C_4$, $D_4$, $E_4$ and $F_4$, the active elements of the slow reacting substance of anaphylaxis (SRS-A). The compounds of Formula I act as inhibitors of the mammalian 5-lipoxygenase enzyme system of the arachidonic acid cascade. This inhibition of the mammalian biosynthesis of leukotrienes indicates that the compositions are useful to treat, prevent or ameliorate, in mammals and especially in humans (1) pulmonary conditions including diseases such as asthma, (2) allergies and allergic reactions such as allergic rhinitis, contact dermatitis, allergic conjunctivitis and the like, (3) inflammation such as arthritis, (4) pain, (5) skin conditions such as psoriasis and the like, and (6) cardiovascular conditions such as angina and the like, and that the compounds are cytoprotective agents.

Thus, the compounds of the present invention may also be used to treat or prevent mammalian (especially, human) disease states such as erosive gastritis; erosive esophagitis; inflammatory bowel disease; ethanol-induced hemorrhagic erosions; hepatic ischemia; noxious agent induced damage or necrosis of hepatic, pancreatic, renal, or myocardial tissue, liver parenchymal damage caused by hepatoxic agents such as $CCl_4$ and D-galactosamine; ischemic renal failure; disease-induced hepatic damage, bile salt induced pancreatic or gastric damage; trauma- or stress-induced cell damage; and glycerol-induced renal failure.

The cytoprotective activity of a compound may be observed in both animal and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay.

A. Ethanol-Induced Gastric Ulcer Assay

Twenty-four hour fasted Sprague-Dawley (S.D.) rats are perorally (p.o.) does with 1.0 ml absolute ethanol. Fifteen to thirty minutes prior to ethanol administration, groups of rats each receive either an aqueous vehicle (aqueous methylcellulose 5% wt.) or the test compound at various doses perorally. One hour later, the animals are sacrificed and stomach mucosa are examined for resulting lesions.

B. Indomethacin-Induced Ulcer Assay

Indomethacin, 10 mg/kg p.o., is used to induce ulcers in 24 hour fasted S. K. rats. Fifteen minutes prior to indomethacin administration, groups of rats each receive either an aqueous vehicle (5% by weight methylcellulose) or the test compound at various doses perorally. Four hours later the animals are sacrifices and stomach mucosa are examined for resulting ulcers.

The magnitude of a prophylactic or therapeutic dose of a compound of formula I will, of course, vary with the nature of the severity of the condition to be treated and with the particular compound of formula I and its route of administration. When a compound of formula I is used in a pharmaceutical composition, the effective concentration in the composition will vary as required by the mode of administration, dosage form and pharmocological effect and level desired. In general, the daily dose range for anti-asthmatic, anti-allergic or anti-inflammatory use and, generally, uses other than cytoprotection lies within the range of from about 0.01 mg to about 20 mg per kg body weight of a mammal. This dosage may be administered in a single or divided individual doses. More or less of the general daily dosage may be necessary depending upon the individual needs of the patient.

The exact amount of a compound of the Formula I to be used as a cytoprotective agent will depend on, inter alia, whether it is being administered to heal damaged cells or to avoid future damage, on the nature of the damaged cells or to avoid future damage, on the nature of the damaged cells (e.g., gastro-intestinal ulcerations vs. nephrotic necrosis), and on the nature of the causative agent. An example of the use of a compound of the Formula I in avoiding future damage would be co-administration of a compound of the Formula I with a non-steroidal anti-inflammatory drug that might otherwise cause such damage (for example, indomethacin). For such use, the compound of Formula I is administered from 30 minutes prior up to 30 minutes after administration of the NSAID (for example, in a combination dosage form). Preferably it is administered prior to or simultaneous with the NSAID.

The effective daily dosage level for compounds of Formulae I inducing cytoprotection in mammals, especially humans, will generally range from about 0.002 mg/kg to about 20 mg/kg, preferably from about 0.02 mg/kg to about 20 mg/kg. The dosage may be administered in single or divided doses.

Any suitable route of administration may be employed for providing a mammal, especially a human, with an effective dosage of a leukotriene antagonist. For example, oral, rectal, transdermal, parenteral, intramuscular, intravenous and the like may be employed. Dosage forms include tablets, troches, dispersions, suspensions, solutions, capsules and the like.

For treating pulmonary conditions such as asthma, the mode of administration may be oral, parenteral, by inhalation, by suppository and the like. Suitable oral dosage forms are tablets, elixirs, emulsions, solutions, capsules, including delayed or sustained release capsules and the like. Parenteral dosage forms include solutions, emulsions and the like. Dosage forms for administration by inhalation including sprays, aerosols and the like. These inhalation formulations may be administered in metered doses ranging from about 0.1 $\mu$g to about 200 $\mu$g, administered as needed.

For treating allergies or allergic reactions, such as allergic conjunctivitis, allergic rhinitis and the like, the Formula I compound may be administered by any conventional mode, e.g., orally, parenterally, topically, subcutaneously, by inhalation and the like. The oral and parenteral dosage forms are the same type as for the pulmonary treatment. The topical application dosage forms include ointments, salves, controlled release patches, emulsions, solutions, thixotropic formulations, powders, sprays and the like. For topical application, the percent by weight active ingredient (Formula I compound) may vary from about 0.001 to about 10%.

For treating inflammation the mode of administration may be oral, parenteral, by suppository and the like. The various dosage forms are the same as those described above.

For treating skin diseases such as psoriasis, atopic dermatitis and the like, oral, topical or parenteral administration is useful. For topical application to the diseased area salves, patches, controlled release patches, emulsions, etc., are convenient dosage forms.

For use as an analgesic, i.e., for treating pain, any suitable mode of administration may be used, e.g., oral, parenteral, by insufflation, by suppository and the like.

For treating cardiovascular conditions such as angina pectoris, etc., any suitable mode of administration, e.g. oral, parenteral, topical, insufflation, etc. and dosage form e.g. pills, liquid formulations, controlled release capsules, controlled release skin patches, etc. may be used.

The pharmaceutical compositions of the present invention comprise a compound of formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethlenediamine, glucosamine, methylglucamine, theobromine, purines, piperazine, piperidine, N-ethylpiperidine, polyamine resins and the like. For a useful discussion of pharmaceutical salts see S. M. Berge et al., Journal of Pharmaceutical Sciences, 66, 1-19 (1977), the disclosure of which is hereby incorporated herein by reference.

The compositions include compositions suitable for oral, rectal, ophthalmic, pummonary, nasal, dermal, topical or parenteral (including subcutaneous, intramuscular and intravenous) administration, although the most suitable route in any given case will depend on the nature an severity of the conditions being treated and on the nature of the active ingredient. They may be conveniently presented in unit dosage form and prepared by any of the methods well-known in the art of pharmacy.

For use where a composition for intravenous administration is employed, a suitable dosage range for anti-asthmatic, anti-inflammatory or anti-allergic use and, generally, uses other than cytoprotection is from about 0.01 mg to about 20 mg (preferably from about 0.1 mg to about 10 mg to about 20 mg) of a compound of formula I per kg of body weight per day and for cytoprotective use from about 0.002 mg to about 20 mg (preferably from about 0.02 mg to about 20 mg and more preferably from about 0.1 mg to about 10 mg) of a compound of Formula I of body weight per day. In the case where an oral composition is employed, a suitable dosage range for anti-asthmatic, anti-inflammatory or anti-allergic use and, generally, uses other than cytoprotection is from about 1 to about 20 of a compound of formula I per kg of body weight per day, preferably from about 5 mg to about 20 mg per kg and for cytoprotective use from about 0.01 mg to about 20 mg (preferably from about 0.1 mg to about 20 mg and more preferably from about 0.1 mg to about 10 mg) of a compound of Formula I per kg of body weight per day.

For administration by inhalation, the compounds of the present invention are conveniently delivered in the form of an aerosol spray presentation from pressurized packs or a nebuliser. The preferred composition form inhalation is a powder which may be formulated as a cartridge from which the powder composition may be inhaled with the aid of a suitable device. In the case of a pressurized aerosol, the dosage unit may be determined by providing a valve to deliver a metered amount.

In practical use, leukotriene antagonists of Formula I can be combined as the active ingredient in intimate admixture with a pharmaceutical carrier according to conventional pharmaceutical compounding techniques and using conventional ingredients, e.g. diluents, carriers, etc. The carrier may take a wide variety of forms depending on the form of preparation desired form administration, e.g., oral or intravenous. In preparing the compositions for oral dosage form, any of the usual pharmaceutical media may be employed, such as, for example, water glycols, oils, alcohols, flavoring agents, preservatives, coloring agents and the like in the case of oral liquid preparations, such as, for example, suspensions, elixirs and solutions; or carriers such as starches, sugars, diluents, granulating agents, lubricants, binders, disintegrating agents and the like in the case of oral solid preparations such as, for example, powders, capsules and tablets and capsules represent the most advantageous oral dosage unit form, in which case solid pharmaceutical carriers are obviously employed. If desired, tablets may be sugar coated or enteric coated by standard techniques.

In addition to the common dosage forms set above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclcsure of which is hereby incorporated herein by reference.

Dosage forms for application to treat the eye are disclosed in U.S. Pat. No. 4,348,398, the disclosure of which is hereby incorporated herein by reference.

Pharmaceutical compositions of the present invention suitable for oral administration and by inhalation in the case of asthma therapy may be presented as discrete units such as capsules, cachets or tablets each containing an predetermined amount of the active ingredient, as a powder or granules or as a solution or suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, lubricating, surface active or dispersing agent. Molded tablets may be made by molding in a suitable machine, a mixture of the powdered compound moistened with an inert liquid diluent. Desirably, each tablet contains from about 25 mg to about 500 mg of the active ingredient and each cachet or capsule contains from about 500 mg of the active ingredient.

The following are examples of representative pharmaceutical dosage forms:

| Injectible Suspension | mg/mL |
|---|---|
| Compound of Formula I | 1–100 |
| Methylcellulose | 5.0 |
| Tween 80 | 0.5 |
| Benzyl alcohol | 9.0 |
| Methyl paraben | 1.8 |
| Propyl paraben | 0.2 |
| Water for injection to a total volume of 1 ml | |

| Aerosol for Oral Inhibition | mg/can (200 doses/can) |
|---|---|
| Compound of Formula I | 2–40 |
| Oleic Acid | 0.2–4.0 |
| Trichloromonofluoro methane | 5,000–8,000 } To a total |
| Dichloromonofluoro methane | 15,000–12,400 } of 20,400 |

| Cream | mg/g |
|---|---|
| Compound of Formula I | 1–100 |
| Cetyl alcohol | 130.0 |
| Sodium Lauryl Sulfate | 15.0 |
| Propylene Glycol | 100.0 |
| Methyl paraben | 1.8 |
| Propyl paraben | 1.2 |
| Purified Water of sufficient quantity to make total 1 g | |

| Ointment | mg/g |
|---|---|
| Compound of Formula I | 1–100 |
| Methyl paraben | 1.8 |
| Propyl paraben | 1.2 |
| Petrolatum of sufficient quantity to make total 1 g | |

| Tablet | mg/tablet |
|---|---|
| Compound of Formula I | 0.2–350 |
| Microcrystalline Cellulose | 0–349.8 |
| Providone | 14.0 |
| Microcrystalline Cellulose | 90.0 |
| Pregelatinized Starch | 43.5 |
| Magnesium Stearate | 2.5 |
| | 500 |

| Capsule | mg/capsule |
|---|---|
| Compound of Formula I | 0.2–350 |
| Lactose Powder | 248.5–598.3 |
| Magnesium Stearate | 1.5 |
| | 600 |

In addition to the compounds of Formula I, the pharmaceutical compositions of the present invention can also contain other active ingredients, such as cyclooxygenase inhibitors, non-steroidal anti-inflammatory drugs (NSAIDS), peripheral analgesic agents such as zomepirac diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams
or a pharmaceutically acceptable salt thereof.

The propionic acid derivatives which may be used comprise: ibuprofen, ibuprufen aluminum, indoprofen, ketoprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —$CH(CH_3)COOH$ or —$CH_2CH_2COOH$ group (which optionally can be in the form of a pharmaceutically acceptable salt group, e.g., —$CH(CH_3)COO^-Na^+$ or —$CH_2CH_2COO^-Na^+$), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structurally related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —$CH_2COOH$ group (which optionally can be in the form of a pharmaceutically acceptable salt group, e.g. —$CH_2COO^-Na^+$), typically attached directly to a ring system, preferably to an aromatic or heteroaromatic ring system.

The fenamic acid derivatives which may be used comprise: mefenamic acid, meclofenamic acid, flufenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

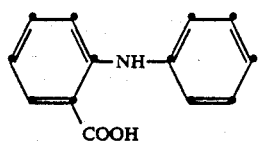

which can bear a variety of substituents and in which the free —COOH group can be in the form of a pharmaceutically acceptable salt group, e.g., —COO$^-$Na$^+$.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

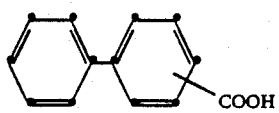

which can bear a variety of substituents and in which the free —COOH group can be in the form of a pharmaceutically acceptable salt group, e.g., —COO$^-$Na$^+$.

The oxicams which can be used in the present invention comprise: piroxicam, sudoxicam, isoxicam and 4-hydroxyl-1,2-benzothiazine 1,1-dioxide 4-(N-phenyl)-carboxamide. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

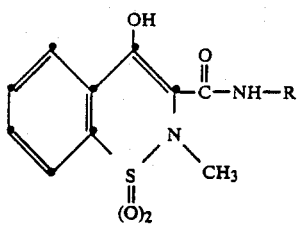

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydanine, beprozin, broperamole, bufezolac, carprofen, cinmetacin, ciproquazone, clidanac, cloximate, dazidamine, deboxamet, delmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin clonixinate, meclofenamate sodium, meseclazone, miroprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

The following NSAIDs, designated by company code number, may also be used: 480156S, AA861, AD1491, AD1590, AFP802, AFP860, AHR6293, AI77B, AP504, AU8001, BAYo8276, BPPC, BW540C, BW755C, CHINOIN 127, CN100, CO893XX, CPP, D10242, DKA9, DV17, EB382, EGYT2829, EL508, F1044, FZ, GP53633, GP650, GV3658, HG/3, ITCl, ITF, ITF182, KB1043, KC8973, KCNTEI6090, KME4, LA2851, LT696, LU20884, M7074, MED15, MG18311, MR714, MR897, MY309, NO164, ONO3144, PR823, PV102, PV108, QZ16, R830, RS2131, RU16029, RU26559, RUB265, SCR152, SH440, SIR133, SIR136, SIR92, SPAS510, SQ27239, ST281, SX1032, SY6001, SaH46798, TA60, TAI901, TEI615, TVX2706, TVX960, TZI615, U60257, UR2310, WY23205, WY41770, YM09561, YM13162, YS1033, and ZK31945.

Finally, NSAIDs which may also be used include the salicylates, specifically aspirin, and the phenylbutazones, and pharmaceutically acceptable salts thereof.

Pharmaceutical compositions comprising the Formula I compounds may also contain inhibitors of the biosynthesis of the leukotrienes such as are disclosed in pending U.S. patent applications Ser. Nos. 539,342, filed Oct. 5, 1983, 459,924, filed Jan. 21, 1983, 539,215, filed Oct. 5, 1983, and 547,161, filed Oct. 31, 1983, which are hereby incorporated herein by reference.

The compounds of the Formula I may also be used in combination with leukotriene antagonists such as those disclosed in copending applications U.S. Ser. Nos. 520,051 and 520,052, filed Aug. 5, 1983 which are hereby incorporated herein by reference and others known in the art such as those disclosed in European Patent Application Nos. 56,172 and 61,800; and in U.K. Patent Specification No. 2,058,785, which are hereby incorporated herein by reference.

Pharmaceutical compositions comprising the Formula I compounds may also contain as the second active ingredient, antihistaminic agents such as benadryl, dramamine, histadyl, phenergan and the like. Alternatively, they may include prostaglandin antagonists such as those disclosed in European Patent Application No. 11,067 or thromboxane antagonists such as those disclosed in U.S. Pat. No. 4,237,160. They may also contain histidine decarboxyase inhibitors such as α-fluoromethylhistidine, described in U.S. Pat. No. 4,325,961. The compounds of the Formula I may also be advantageously combined with an H$_1$ or H$_2$-receptor antagonist, such as for instance cimetidine, ranitidine, terfenadine, famotidine, aminothiadiazoles disclosed in EP No. 81102976.8 and like compounds, such as those disclosed in U.S. Pat. Nos. 4,283,408; 4,362,736; 4,394,508; European Patent Application No. 40,696 and a pending application, U.S. Ser. No. 301,616, filed Sept. 14, 1981. The pharmaceutical compositions may also contain a K$^+$/H$^+$ATPase inhibitor such as omeprazole, disclosed in U.S. Pat. No. 4,255,431, and the like. Each of the references referred to in this paragraph is hereby incorporated herein by reference.

The following examples illustrate the preparation of several compounds of the instant invention. No limitation is intended by these example, they merely serve to illustrate the inventive concept. All temperatures are in degrees Celsius.

EXAMPLE 1

2-Amino-2-carboxydiphenylsulfide hydrochloride

A mixture of o-iodobenzoic acid (25 g,100 mmoles), potassium hydroxide (26.3 g), o-amino thiophenol (14 g,110 mmoles) and copper metal (5.24 g,100 mmoles) in water (150 ml) was refluxed under nitrogen for 2 hours. The reaction mixture was filtered and the filtrate was acidified with concentrated hydrochloric acid. The resulting solid was filtered, washed with water and air-dried to yield the title compound, m.p. 235° (dec.).

Elemental analysis, C: 55.41; H: 4.29; N: 4.97; S: 11.37; Cl: 12.58. Found, C: 55.67; H: 4.61; N: 4.82; S: 10.43; Cl: 12.26

EXAMPLE 2

2-Amino-5-methoxy-2'-carboxydiphenylsulphide hydrochloride

Following the conditions of Example 1, but substituting 2-amino-5-methoxythiophenol for o-aminothiophenol, the title compound was obtained, m.p. 220–225° (dec.).

EXAMPLE 3

2 Amino-5-hydroxy-2'-carboxydiphenylsulphide hydrobromide

A solution of 2-amino-5-methoxy-2'-carboxydiphenylsulphide hydrochloride (2.0 g,6.4 mmoles) in 48% hydrobromic acid (75 ml) was refluxed for 5 hours. The mixture was cooled to room temperature and the solids were filtered, washed with water and air-dried to give the title compound, m.p. 278–283°.

Elemental analysis, C: 45.62; H: 3.53; N: 4.09; S: 9.36. Br: 23.34. Found, C: 45.77; H: 4.03; N: 4.31; S: 8.80; Br: 23.57.

EXAMPLE 4

2-Amino-4-chloro-5-methoxy-2'-caboxydiphenylsulfide hydrochloride

Following the conditions of Example 1, but substituting 2-amino-4-chloro-5-methoxythiophenol for o-aminothiophenol, the title compound, m.p. 210–215° (dec.), was obtained.

Elemental analysis, C: 48.56; H: 3.28; N: 4.04; S: 9.26; Found C: 48.04; W: 3.31; N: 3.93;S: 9.33.

EXAMPLE 5

10,11-Dihydro-11-oxodibenzo[b,f][1,4]thiazepin

2-Amino-2'-carboxydiphenylsulphide hydrochloride (0.5 g,1.8 mmoles) was heated at 230° for 30 minutes under a nitrogen atmosphere. The solid was recrystallized from ethyl acetate to yield the title compound, m.p. 265–267°.

Elemental analysis, C: 68.64; H: 4.07; N: 6.16; S: 14.10. Found: C: 68.64; H: 4.22; N:6.30; S: 14.04.

EXAMPLE 6

10,11-Dihydro-7-methoxy-11-oxodibenzo[b,f][1,4]-thiazepin

Following the conditions of Example 5, pyrolysis of 2-amino-4-methoxy-2'-carboxydiphenylsulfide hydrochloride gave the title compound, m.p. 240–241°.

Elemental analysis, C: 65.35; H: 4.30; N: 5.44; S: 12.46. Found, C: 65.16; H: 4.24; N: 5.28; S: 11.45.

EXAMPLE 7

10,11-Dihydro-7-hydroxy-11-oxodibenzo[b,f][1,4]-thiazepin

Following the conditions of Example 5, pyrolysis of 2-amino-4-hydroxy-2'-carboxydiphenyl sulfide hydrobromide gave the title compound, m.p. 265–267°.

Elemental analysis, C: 64.18; H: 3.72; N: 5.75; S: 13.17. Found, C: 63.47; H:3.52; N:5.45; S:13.16.

EXAMPLE 8

10,11-Dihydro-8-chloro-7-methoxy-11-oxodibenzo[b,f][1,4]thiazepin

Following the conditions of Example 5, pyrolysis of 2-amino-4-chloro-5-methoxy-2'-carboxydiphenylsulphide hydrochloride gave the title compound, m.p. 280–283°.

Elemental analysis, C: 57.63; H: 3.45; N: 4.80; S: 10.98; Cl: 12.15. Found, C: 57.53; H: 3.43; N: 4.93; S: 11.25; Cl: 12.34.

EXAMPLE 9

2-Amino-4-chloro-5-hydroxy-2'-carboxydiphenylsulphide hydrobromide

Following the conditions of Example 3, hydrolysis of 2-amino-4-chloro-5-methoxy-2'-carboxydiphenylsulfide hydrochloride gave the title compound, m.p. 210–215° (dec.).

Elemental analysis, C: 41.45; H: 2.94; N: 3.71; S: 8.51; Cl: 9.41; Br: 21.21. Found, C: 41.45; H: 2.92; N: 3.46; S; 8.49; Cl: 9.11; Br: 20.83.

EXAMPLE 10

10,11-Dihydro-8-chloro-7-hydroxy-11-oxodibenzo[b,f][1,4]thiazepin

Following the conditions of Example 5, pydrolyis of 2-amino-4-chloro-5-methoxy-2'-carboxydiphenylsulfide hydrobromide gave the title compound mp. 295°–298° (dec.).

Elemental analysis, C: 56.22; H: 2.90; N: 11.54; Cl: 12.76. Found, C: 55.94; H: 3.02; N: 5.19; S: 11.62; Cl: 12.24.

EXAMPLE 11

10,11-Dihydro-7-hydroxydibenzo[b,f][1,4]thiazepin

A mixture of 10,11-dihydro-7-hydroxy-11-oxodibenzo[b,f][1,4]thiazepin (4.5g,18.5 mmoles) and lithium aluminum hydride (3.5g,92.5 mmoles) in tetrahydrofuran (200 ml) and N-ethylmorpholine (100 ml) was refluxed for 18 hours. The reaction mixture was decomposed by the addition of 12 ml of a saturated solution of ammonium chloride and 33 ml of 1M sodium bicarbonate. The mixture was filtered and the salts were washed with methanol. The filtrate was evaporated to dryness and the residue was extracted several times with ether. Chromatography of the residue on silica gel, eluting with 5% methanol in chloroform, afforded the title compound, m.p. 172°–174°.

Elemental analysis, C: 68.09; H: 4.83; N: 6.10: S: 13.98. Found, C: 68.31; H: 4.58; N: 6.08; S: 14.15.

EXAMPLE 12

10,11-Dihydro-7-methoxydibenzo[b,f][1,4]thiazepin (title compound) and 10,11-dihydro-11-hydroxy-7-methoxydibenzo[b,f][1,4]-thiazepin (major compound)

Following the conditions of Example 11, the reduction of 10,11-dihydro-7-methoxy-11-oxodibenzo [b,f][1,4]thiazepin gave the title compound, m.p. 88°–90°. The major product formed in this reaction was 10,11-dihydro-11-hydroxy-7-methoxydibenzo[b,f][1,4]-thiazepin, m.p. 153°–156°.

Elemental analysis of title compound, C: 69.10; H: 5.38; N: 5.75; S: 13.17. Found, C: 69.16; H: 5.32; N: 5.94; S: 12.64.

Elemental analysis of major compound, C: 64.84; H: 5.05 N: 5.40; S: 12.36. Found, C: 69.89; H: 4.72: N: 5.75: S: 12.56.

EXAMPLE 13

10,11-Dihydro-10-formyl-7-methoxydibenzo [b,f][1,4]thiazepin

To a solution of 10,11-dihydro-7-methoxydibenzo[b,f][1,4]thiazepin (6.5 g,26.6 mmoles) in tetrahydrofuran (100 ml) was added 5 ml of formic acetic anhydride. The mixture was stirred at from 0 to 5° C. for 15 minutes. The mixture was then concentrated in vacuo. The residue was taken up in ether and a solid crystallized out. The solid was filtered, washed with ether and air-dried to give the title compound, m.p. 98°–100°.

Elemental analysis, C: 66.39; H: 4.82; N: 5.16; S: 11.81. Found, C: 65.92; H: 4.90; N: 4.81; S: 11.94.

EXAMPLE 14

10,11-Dihydro-10-methyl-7-methoxydibenzo[b,f][1,4]-thiazepin

Following the conditions of Example 11, the reduction of 10,11-dihydro-10-formyl-7-methoxydibenzo [b,f][1,4]thiazepin gave the title compound, m.p. 148° (dec.).

Elemental analysis, C: 61.31; H: 5.48; N: 4.76; S: 10.91; Cl: 12.06. Found, C: 61.06; H: 5.70; N: 5.02; S: 10.83; Cl: 11.62.

The major compound (65%) produced in this reaction was 10,11-dihydro-7-methoxydibenzo [b,f][1,4]thiazepin.

EXAMPLE 15

7-Hydroxydibenzo[b,f][1,4]thiazepin-5,5-dioxide

A mixture of 10.11-dihydro-7-hydroxydibenzo [b,f][1,4]thiazepin (2.2 g,10 mmoles) and m-chloroperbenzoic acid (3.4 g,20 mmoles) in methylene chloride (250 ml) was stirred at 0° C. for 1 hour. The reaction mixture was treated with 4 g of calcium hydroxide for 15 minutes and was then filtered. The filtrate was chromatographed on silica gel, eluting with 5% methanol in chloroform, to yield the title compound, m.p. 202° (dec.).

Elemental analysis, C: 60.22; H: 3.49; N: 5.40; S: 12.36. Found, C: 60.22; H: 3.43; N: 5.54; S: 11.93.

EXAMPLE 16

10,11-Dihydro-10-methyl-7-methoxydibenzo[b,f][1,4]-thiazepin-5-oxide

Following the conditions of Example 15, the oxidation of 10,11-dihydro-10-methyl-7-methoxy dibenzo [b,f][1,4]thiazepin with 1 equivalent of m-chloroperbenzoic acid afforded the title compound, m.p. 105–109°.

Elemental analysis, C: 65.90; H: 5.53; N: 5.12; S: 11.72. Found, C: 66.08; H: 5.69; N: 4.87; S: 11.41.

EXAMPLE 17

2-i-Propylamino-5-Methoxythiophenol (a) Preparation of 5-methoxy-2,2-dimethyl benzo thiazolidine A solution of 5-methoxy-2-amino thiophenol (15.5 gm 0.1 mole) in 25 ml acetone was stirred overnight at room temperature. The volatiles were removed in vacuo and the residue was distilled. The 5-methoxy-2.2-dimethylbenzothiazolidine was isolated in 94% yield b.p. 142° C. /0.3 mm Hg.

(b) Preparation of 2-i-Propylamino-5-methoxythiophenol

To 5-methoxy-2,2-dimethylbenzothiazolidine (14.6 gm; 75 mmoles) in 50 ml dimethoxyethane and 5 ml isopropanol was added sodium borohydride (4.0 gm; 0.1 mole). The reaction mixture was stirred at room temperature for 1 hour. The mixture was then poured over 5 N acetic acid, extracted with methylene chloride, washed with brine, dried (Na₂SO₄) and concentrated in vacuo. The residue was recrystallized from hexane to yield the title compound, m.p. 68°–69° C. in nearly quantitative yield.

EXAMPLE 18

2-i-Propylamino thiophenol (a) Preparation of 2,2-dimethylbenzothiazolidine

Using the method of Example 17a reaction of o-aminothiophenol with acetone yielded 53% of 2,2-dimethylbenzothiazolidine b.p. 120° C./10.2 mm Hg.

(b) Preparation of 2-i-propylaminothiophenol

Use the method of Example 17b, reaction of 2,2-dimethylbenzothiazolidine with sodium borohydride to obtain the title compound.

The claims to the invention follow.

What is claimed is:

1. Compounds having the formula:

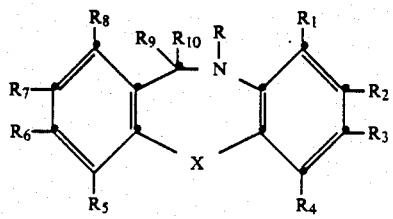

wherein
X is thio, sulfonyl or sulfinyl
R is $C_1$ to $C_{20}$ alkyl which may be straight chain, branched chain or cyclic;
$R_1$ to $R_8$ are each independently selected from hydrogen, hydroxy, halogen including F, Cl, Br, I, —OR, OCOR, NHR, N[R]$_2$, NO$_2$, SR, SOR, SO$_2$R, SO$_2$NHR, SO$_2$N(R)$_2$, CN, COOR, CF$_3$, CF$_3$S, CHO, COR, CH$_2$OR, R, phenyl, phenyl substituted by one or more groups selected from OH, C$_1$ to C$_6$-alkyl, COOR, CN, NO$_2$, CF$_3$, SR, NHR or N(R)$_2$;

R$_9$ is H or OH;

R$_{10}$ is H, or together

R$_9$ and R$_{10}$ form a double bonded oxo group;

and pharmaceutically acceptable salts thereof.

2. A compound of claim 1 having the formula:

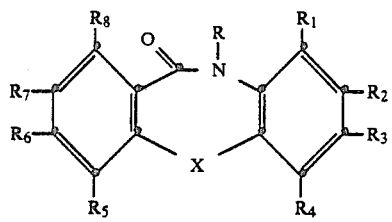

wherein R, R$_1$, R$_2$, R$_3$, R$_4$, R$_5$, R$_6$, R$_7$, R$_8$ and X are as defined in claim 1

3. A compound of claim 1 having the formula:

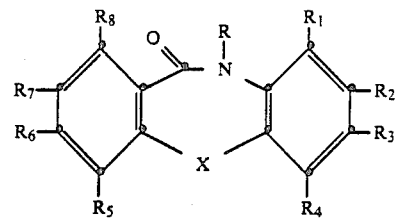

wherein R is C$_1$ to C$_4$-alkyl, R$_1$, R$_2$, R$_3$, R$_4$, R$_5$, R$_6$, R$_7$, R$_8$ and X are as defined in claim 1.

4. 10,11-Dihydro-7-methoxy-11-oxodibenzo[b,f][1,4]thiazepin.

5. 10,11-Dihydro-8-chloro-7-methoxy-11-oxodibenzo[b,f][1,4]thiazepin.

6. 10,11-Dihydro-8-chloro-7-hydroxy-11-oxodibenzo[b,f][1,4]thiazepin.

7. 10,11-Dihydro-7-hydroxydibenzo[b,f][1,4]thiazepin.

8. 10,11-Dihydro-7-methoxydibenzo[b,f][1,4]thiazepin.

9. 10,11-Dihydro-10-formyl-7-methoxydibenzo[b,f][1,4]thiazepin.

10. 10,11-Dihydro-10-methyl-7-methoxydibenzo[b,f][1,4]thiazepin.

11. 10,11-Dihydro-10-methyl-7-methoxydibenzo[b,f][1,4]thiazepin-5-oxide.

* * * * *